(12) United States Patent
Lindner

(10) Patent No.: US 8,337,558 B2
(45) Date of Patent: Dec. 25, 2012

(54) VERTEBRAL BODY REPLACEMENT IMPLANT

(75) Inventor: Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 530 days.

(21) Appl. No.: 12/321,764

(22) Filed: Jan. 22, 2009

(65) Prior Publication Data

US 2009/0192612 A1    Jul. 30, 2009

(30) Foreign Application Priority Data

Jan. 29, 2008   (DE) .......................... 10 2008 006 492

(51) Int. Cl.
*A61F 2/44* (2006.01)
(52) U.S. Cl. .................................. 623/17.15; 623/17.11
(58) Field of Classification Search ............... 623/17.11, 623/17.16; 606/279
See application file for complete search history.

(56) References Cited

U.S. PATENT DOCUMENTS

| 5,989,290 | A  | * | 11/1999 | Biedermann et al. ....... 623/17.11 |
| 6,176,881 | B1 | * | 1/2001  | Schar et al. ................ 623/17.11 |
| 6,200,348 | B1 |   | 3/2001  | Biedermann et al. |
| 6,524,341 | B2 |   | 2/2003  | Lang et al. |
| 2002/0161441 | A1 |   | 10/2002 | Lang et al. |
| 2005/0060036 | A1 |   | 3/2005  | Schultz et al. |
| 2006/0058877 | A1 | * | 3/2006  | Gutlin et al. ................ 623/17.11 |
| 2007/0093901 | A1 |   | 4/2007  | Grotz et al. |

FOREIGN PATENT DOCUMENTS

| DE | 198 04 765     | 8/1999 |
| DE | 10 2005 022 920 | 11/2006 |
| EP | 1 121 075      | 8/2001 |

* cited by examiner

*Primary Examiner* — Kevin T Truong
*Assistant Examiner* — Larry E Waggle, Jr.
(74) *Attorney, Agent, or Firm* — Lipsitz & McAllister, LLC

(57) ABSTRACT

In a vertebral body replacement implant having a bottom locating part for positioning against a lower vertebral body and having a top locating part for positioning against an upper vertebral body, wherein both locating parts are steplessly displaceable relative to one another along a displacement path so that the height of the vertebral body replacement implant is variable, having a clamping device for fixing the two locating parts in any desired intermediate position along the displacement path, which clamping device comprises a clamping element that is mounted on one locating part so as to be variable in position and can be pressed towards a clamping face on the other locating part, in order to improve the clamping action it is proposed that the clamping face is inclined slightly relative to the displacement path, so that when the locating parts are pushed together the clamping face moves progressively closer to the clamping element.

16 Claims, 5 Drawing Sheets

VERTEBRAL BODY REPLACEMENT IMPLANT

The present disclosure relates to the subject matter disclosed in German patent application 10 2008 006 492.0 of Jan. 29, 2008, which is incorporated herein by reference in its entirety and for all purposes.

BACKGROUND OF THE INVENTION

The invention relates to a vertebral body replacement implant having a bottom locating part for positioning against a lower vertebral body and having a top locating part for positioning against an upper vertebral body, wherein both locating parts are steplessly displaceable relative to one another along a displacement path so that the height of the vertebral body replacement implant is variable, having a clamping device for fixing the two locating parts in any desired intermediate position along the displacement path, which clamping device comprises a clamping element that is mounted on one locating part so as to be variable in position and can be pressed towards a clamping face on the other locating part.

Such a vertebral body replacement implant is described for example in DE 10 2005 022 920 B4. By means of a hydraulic medium the two locating parts can be pushed steplessly apart from one another and, for fixing an obtained spacing of the two locating parts, in this known vertebral body replacement implant by means of a adjusting screw a clamping element in one of the two locating parts can be advanced in such a way towards the other locating part that at a clamping face of the other locating part a clamping of the two locating parts is effected. In this way, a stepless adjustment and a maintaining of the height of the entire vertebral body replacement implant is possible.

Proceeding from this background art the underlying object of the invention is to improve the clamping action for fixing the spacing of the two locating parts.

SUMMARY OF THE INVENTION

In a vertebral body replacement implant of the type described in the introduction, this object is achieved according to the invention in that the clamping face is inclined slightly relative to the displacement path, so that when the locating parts are pushed together the clamping face moves progressively closer to the clamping element.

The effect achieved by this inclination of the clamping face is that the clamping action is intensified when the two locating parts are pushed together. The result is an additional safeguard against an unintended pressing-together of the two locating parts. Even if the clamping action of the clamping element during the initial fixing of the two locating parts were to prove inadequate or diminish in the course of time, this would lead only to the locating parts moving very slightly closer to one another because, owing to the inclination of the clamping face, this pushing-together would inevitably generate an increase of the clamping force, i.e. the inadequate clamping force that leads to an undesired movement of the two locating parts closer to one another is immediately compensated by this very movement, with the result that the two locating parts in this situation too may move only minimally towards one another.

On the other hand, during pressing of the clamping element against the clamping face the very slight inclination of the clamping face prevents the locating elements from being pressed apart. With a very much greater inclination of the clamping face such a displacement might occur because of the oblique slope of the clamping face, but this is not the case with an only very slight inclination of the clamping face relative to the displacement path. The inclination of the clamping face incidentally is preferably between 1° and 10°, in particular between 1° and 3°.

It is advantageous if the clamping face is flat.

In a first preferred embodiment it is provided that the clamping element has a locating face, which faces the clamping face and the inclination of which differs from that of the clamping face in such a way that the clamping element presses only at the edge of the locating face against the clamping face. In this embodiment, therefore, the clamping element abuts against the clamping face not with the full surface of its locating face but only in a very small edge region, which consequently generates a very high surface pressure between the clamping element, on the one hand, and the clamping face, on the other hand, when the clamping element is pressed against the clamping face. In particular, the clamping element may have a locating face that is disposed parallel to the displacement path, so that the angle between clamping face and locating face corresponds to the angle of inclination between the clamping face and the displacement path.

In another preferred embodiment, on the other hand, it is provided that the clamping element has a locating face, which faces the clamping face and moves into abutment with the clamping face and which is so small that the locating face, as it is pressed against the clamping face, digs into the clamping face. Such a notch effect leads to a strengthened fixing of the two locating parts relative to one another, the digging of the locating face into the clamping face therefore very effectively preventing the locating parts from moving closer to one another. Either the locating face may be configured to be very small or a very small effective contact surface necessarily arises when the locating face has an inclination differing from that of the clamping face.

The clamping element may be for example an attachment screw.

In another preferred embodiment it is provided that the clamping element has a locating face, which faces the clamping face and of which the inclination relative to the displacement path corresponds to the inclination of the clamping face. In this case, therefore, clamping face and locating face have the same inclination relative to the displacement path and, when the clamping element is pressed on, come with their full surface area into mutual abutment. This also leads to a very effective fixing of the two locating parts and reliably prevents an unintended pushing-together of the locating parts.

In a particularly preferred embodiment it is provided that the clamping element is guided displaceably in a guide of the one locating part and that for displacement of the clamping element an adjusting screw is provided, which extends into the guide and abuts against the clamping element.

In this case, the clamping element may in particular take the form of a ring or a circular-cylindrical disk, the central axis of which is disposed parallel to the direction of displacement of the clamping element in the guide.

It is particularly advantageous if there is disposed on one locating element a laterally projecting guide connection piece, the inner wall of which forms the guide for the clamping element and into which the adjusting screw may be screwed.

In a further preferred embodiment it is provided that a hydraulic conduit extends through a through-channel of the adjusting screw and through a central opening of the clamping element into the interior of the one locating element. Through this hydraulic conduit a hydraulic medium, for example a physiological saline, can be introduced into the interior of the vertebral body replacement implant, this hydraulic medium then being used in the manner of a hydraulic piston-cylinder unit to push the two locating parts apart from one another.

In a preferred embodiment, the clamping face of the other locating part may be formed by the base of a lateral recess in a side wall of the other locating part.

It is particularly advantageous if both the locating parts are displaceable telescopically relative to one another along the displacement path.

The following description of preferred embodiments of the invention serves in connection with the drawings to provide a detailed explanation.

DETAILED DESCRIPTION OF THE INVENTION

Figure 1:
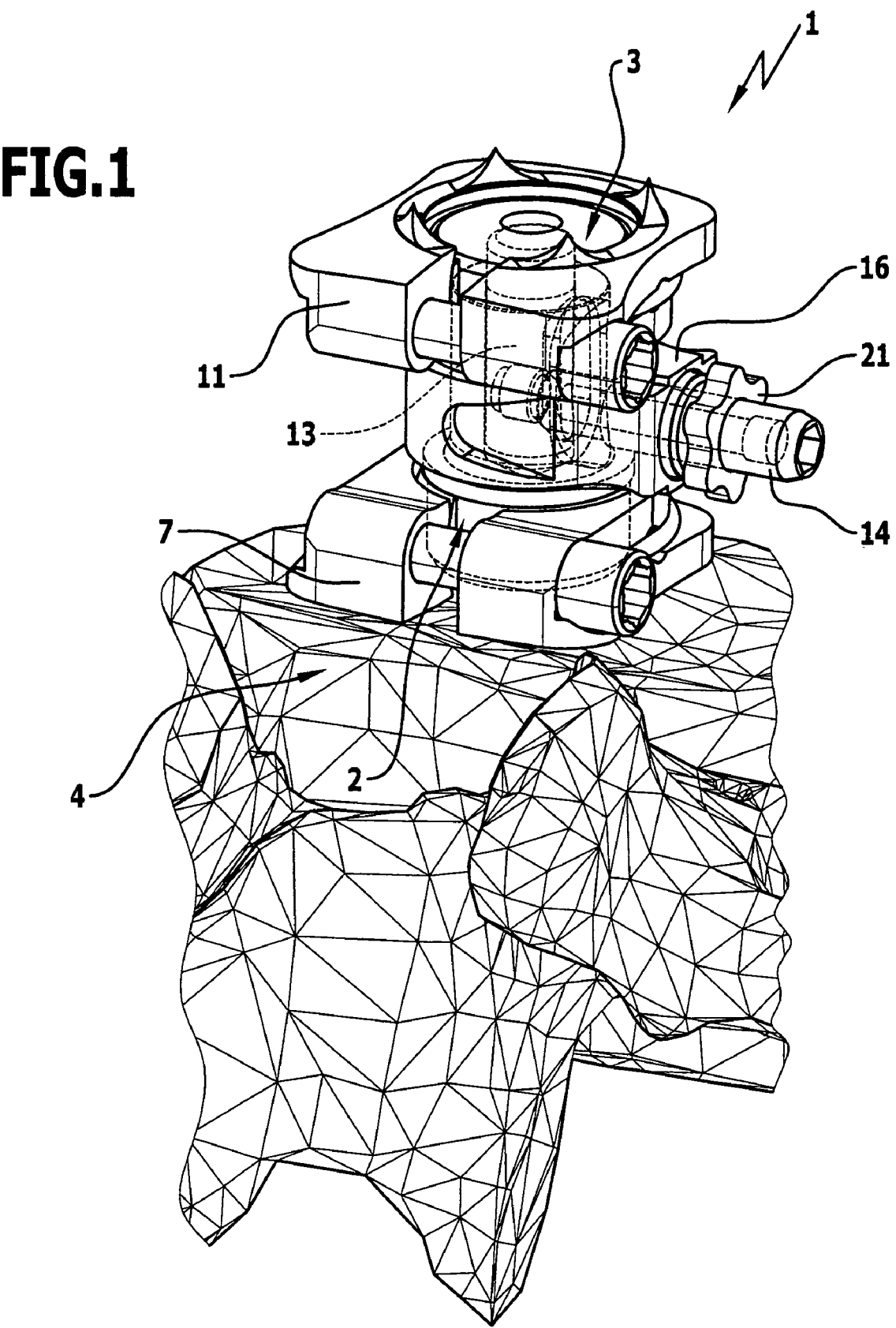
FIG. 1: is a perspective view of a vertebral body replacement implant with a vertebral body disposed below the implant.

The vertebral body replacement implant 1 shown in the drawings comprises a bottom locating part 2 and a top locating part 3. The vertebral body replacement implant 1 is intended to replace one or more vertebral bodies and is positioned by its bottom locating part 2 against a lower vertebral body 4 and by its top locating part 3 against an upper vertebral body that is not shown in the drawings. In this way, the two vertebral bodies adjacent to the vertebral body replacement implant 1 may be braced relative to one another.

The bottom locating part 2 comprises a circular-cylindrical base 5 that is adjoined at the top by a circular-cylindrical portion 6, the outside diameter of which is smaller than the outside diameter of the base 5. Fastened to the base 5 is a bottom support plate 7, which is shown only in FIG. 1 and for the sake of greater clarity has been omitted from the representations of FIGS. 2 to 5.

The top locating part 3 comprises a cylinder 8, which is closed at its top end 9 and open at its bottom end 10. As in the case of the bottom locating part 2, there is disposed on this cylinder 8 a top support plate 11, which is likewise shown only in FIG. 1 and for greater clarity has been omitted from FIGS. 2 to 5.

The outside diameter of the circular-cylindrical portion 6 of the bottom locating part 2 corresponds to the inside diameter of the cylinder 8, the portion 6 engaging telescopically into the interior of the cylinder 8 so that the two locating parts 2 and 3 are displaceable telescopically relative to one another, thereby altering the height of the vertebral body replacement implant 1.

In order to displace the two locating parts 2 and 3 relative to one another, the interior 12 formed by the top locating part 3, on the one hand, and the bottom locating part 2 mounted in a telescopically displaceable manner in the top locating part 3, on the other hand, can be filled with a hydraulic medium, for example with physiological saline. For this purpose, the portion 6 of the bottom locating part 2 and the inner wall of the top locating part 3 are sealed relative to one another, for example by means of a seal that is not specifically shown in the drawings.

Figure 2:
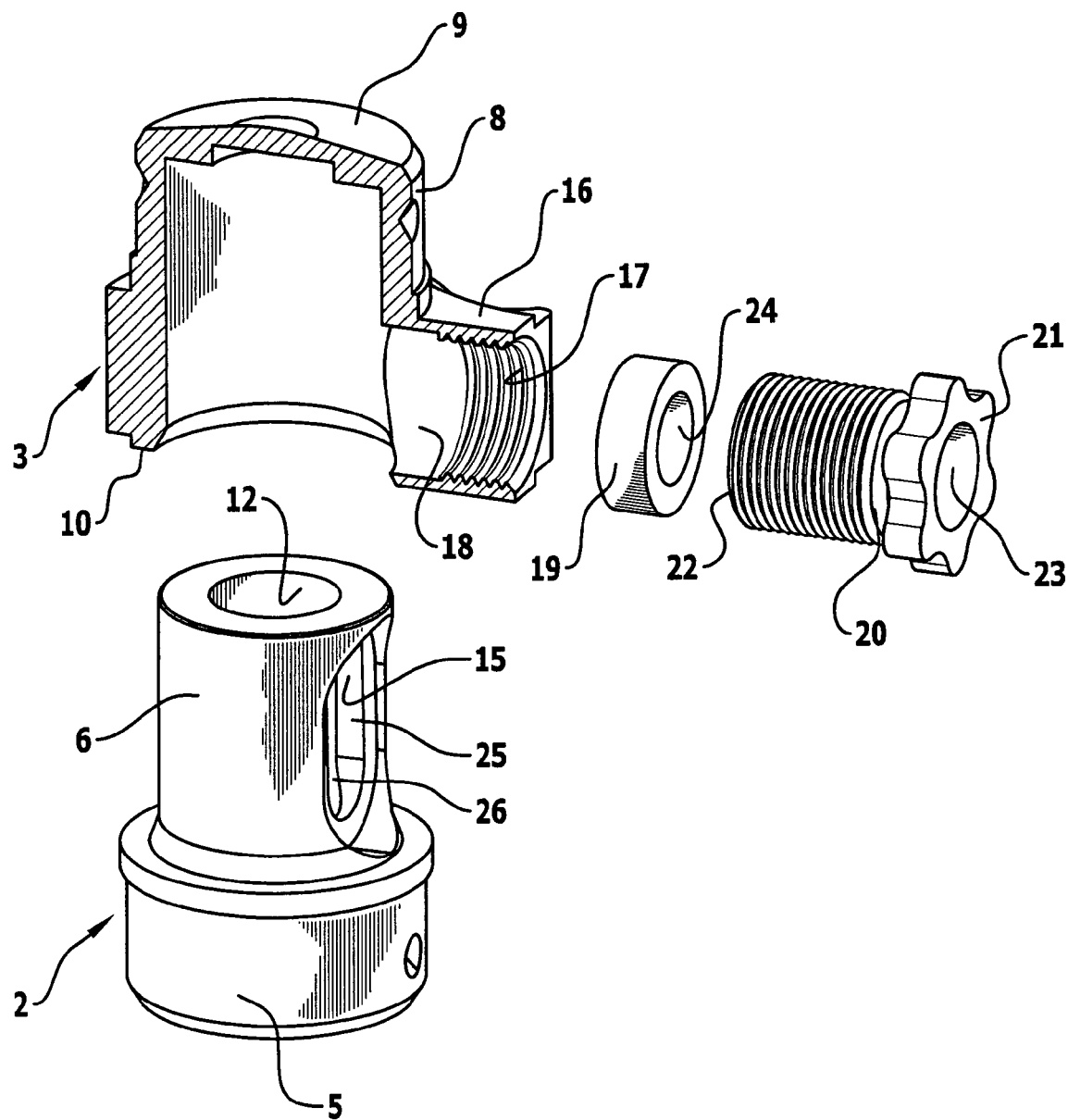
FIG. 2: is an exploded view of the vertebral body replacement implant of FIG. 1 without locating plates and without a charging connection piece for a hydraulic medium.

To introduce the hydraulic medium into the interior 12, there is inserted in the interior 12 a tube piece 13, which is disposed coaxially with the portion 6 and opening into which is a charging tube 14 that extends radially into the vertebral body replacement implant 1 (FIG. 1). This charging tube passes through an elongate opening 15 in the side wall of the portion 6 as well as a guide connection piece 16, which is moulded laterally onto the top locating part 3 and from which the charging tube projects. This guide connection piece 16 in its radially outer region carries an internal thread 17 and in its radially inner region forms a smooth inner wall 18 (FIG. 2). In the region with the smooth inner wall 18 an annular clamping element 19 is guided so as to be displaceable parallel to the longitudinal direction of the guide connection piece 16, and screwed into the internal thread 17 is an adjusting screw 20, which has a rosette-shaped head 21 and of which the opposite end 22 to the head 21 is supported against the clamping element 19. The adjusting screw 20 has a through-channel 23, and a central opening 24 aligned with this channel 23 is provided in the clamping element 19, the charging tube 14 projecting through this opening 24 and the channel 23 and therefore being directly surrounded by the clamping element 19 and the adjusting screw 20.

In the side wall of the portion 6 there is disposed in the region of the elongate opening 15 a recess 25 that projects laterally from the elongate opening 15. The base 26 of this recess 25 forms a clamping face, against which the clamping element 19 is pressed when the adjusting screw 20 is screwed into the internal thread 17. The base is of a flat design and its width corresponds to the width of the clamping element 19. In relation to the direction of displacement of the two locating parts 2 and 3 the base 26 is slightly inclined, with the result that at the bottom end of the portion 6 the distance of the base 26 from the centre line of the portion 6 is greater than at the top end. As a result of this inclination of the base 26, the distance of the base 26 from the clamping element 19 decreases as the two locating parts 2, 3 are moved closer to one another.

The inclination of the base 26 relative to the direction of displacement is slight and is in the order of magnitude of between 1° and 10°, in particular between 1° and 3°.

In the embodiment shown in the drawings, the locating face 27 of the clamping element 19 facing the base 26 extends parallel to the direction of displacement, i.e. is inclined relative to the base 26 by the same angle as the base 26 is inclined relative to the direction of displacement. When the clamping element 19 advances as a result of screwing-in of the adjusting screw 20, the locating face 27 therefore makes contact only in the bottom edge region with the base 26 forming the clamping face, as is apparent from the representation of FIG. 5. The locating face is consequently very small and the contact occurs in the region of the edge of the clamping element 19. Thus, during the powerful pressing of the clamping element 19 against the base 26 it is possible for the locating face 27 to dig slightly into the base 26 and hence reliably prevent the two locating parts 2 and 3 from moving any closer to one another.

In another embodiment that is not shown in the drawings, the locating face 27 may alternatively extend parallel to the base 26, with the result that a full-surface abutment is achieved when the clamping element 19 is advanced towards the base 26.

Figure 3:
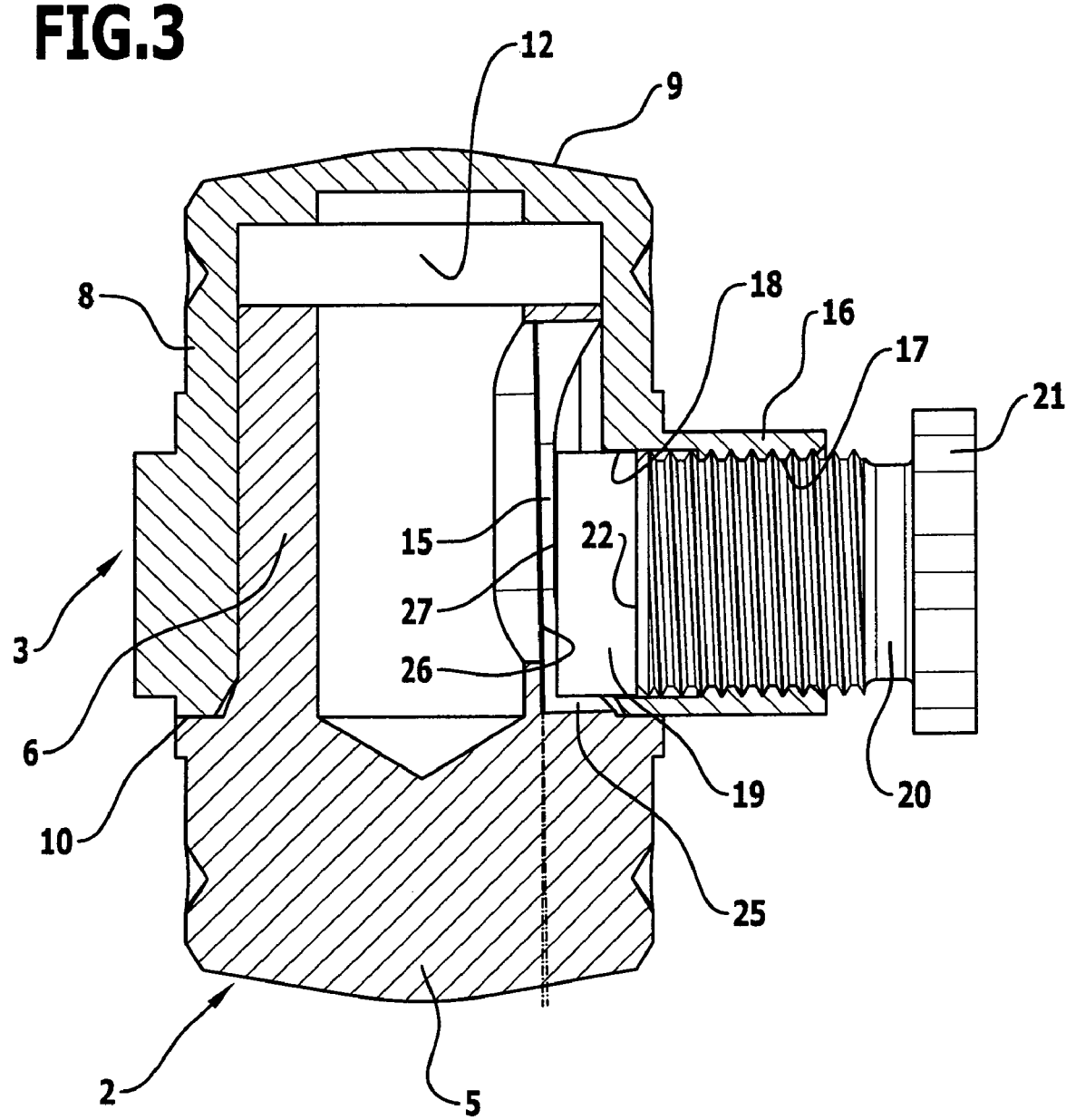
FIG. 3: is a cross-sectional view of the parts of the vertebral body replacement implant of FIG. 2 in the assembled state with the locating parts fully pushed together and with the clamping device released.
Figure 4:
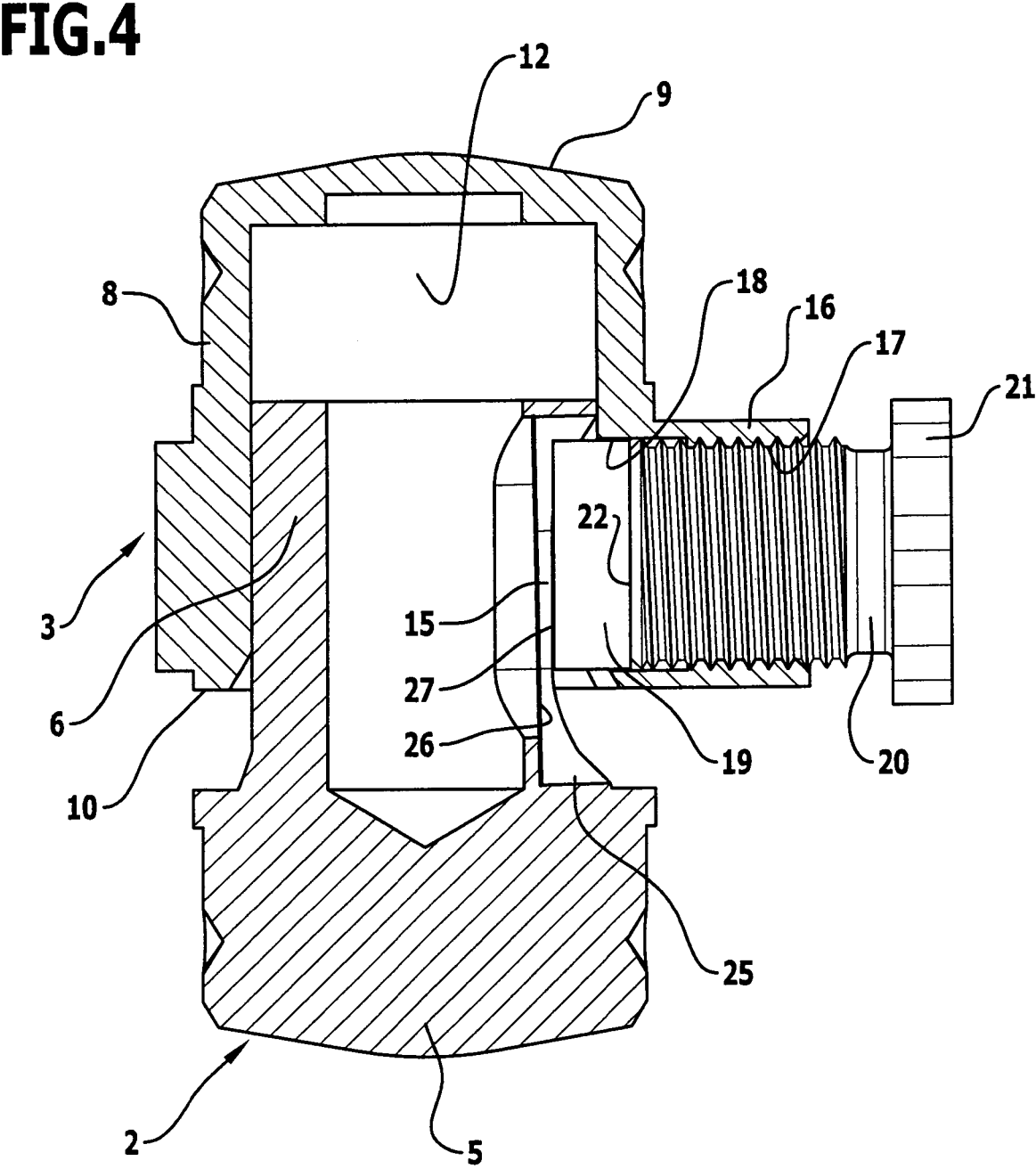
FIG. 4: is a view similar to FIG. 3 with the locating parts pushed apart from one another and the clamping device released
Figure 5:
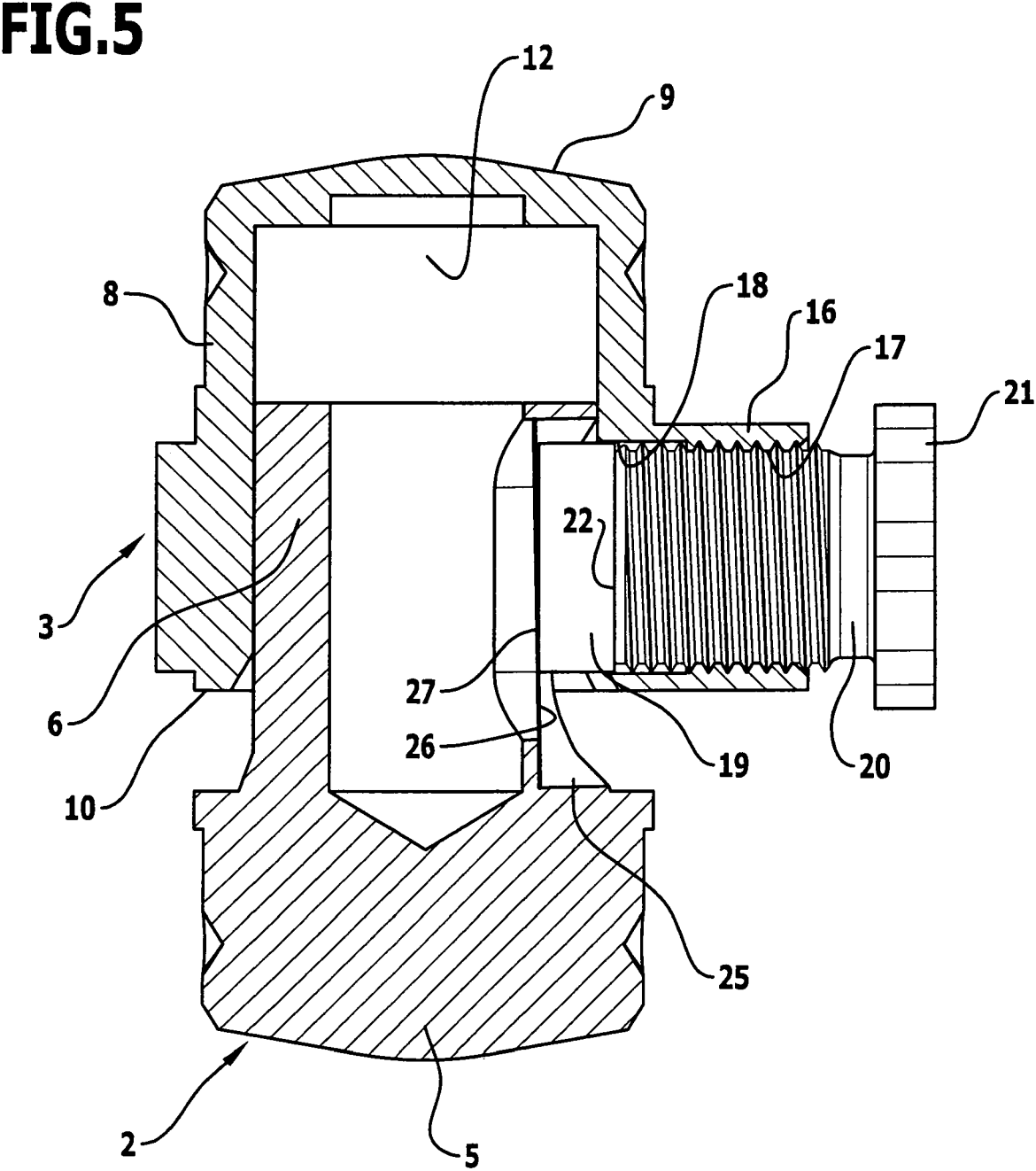
FIG. 5: is a view similar to FIG. 4 with the clamping device clamped.

In order to fit the vertebral body replacement implant 1, it is initially inserted with the locating parts pushed together and without abutment of the clamping element 19 with the base 26 (FIG. 3).

After insertion, by introducing a hydraulic medium into the interior 12 the two locating parts 2, 3 are pushed apart from one another until the requisite height of the vertebral body replacement implant 1 is reached. In a subsequent step, the adjusting screw 20 is screwed into the internal thread 17, with the result that the clamping element 19 is pressed powerfully against the base 26. Thus, the relative position of the two locating parts 2, 3 is fixed. The interior 12 can then be emptied, the height of the vertebral body replacement implant 1 thus adjusted and fixed then being maintained.

Even in the event of high forces pressing the two locating parts 2, 3 towards one another, there is no danger of an unintentional displacement of these locating parts 2, 3 towards one another. Any movement of the two locating parts 2 and 3 towards one another namely leads, because of the inclination of the base 26 relative to the direction of displacement, to an immediate increase of the clamping forces of the clamping element 19 on the base 26 and therefore counteracts this unintended movement. The inclination of the base 26 therefore provides an additional safeguard for the eventuality that the clamping forces of the clamping element 19 should for some reason prove inadequate. When the two locating parts 2 and 3 are pressed together, these clamping forces automatically increase and hence prevent the locating parts 2, 3 from being pressed any closer together.

The invention claimed is:

1. A vertebral body replacement implant comprising:
   a bottom locating part for positioning against a lower vertebral body,
   a top locating part for positioning against an upper vertebral body, both locating parts being steplessly displaceable and steplessly fixable relative to one another along a displacement path so that a height of the vertebral body replacement implant is variable,
   a clamping device for fixing the two locating parts in any desired intermediate position along the displacement path in a stepless manner, said clamping device having a clamping element that is mounted on one of the bottom and top locating parts so as to be variable in position and can be pressed towards a clamping face on the other of the bottom and top locating parts,
   wherein:
      the displacement path comprises substantially an entire length of overlapping portions of the two locating parts;
      the clamping face is flat;
      the clamping element has a flat locating face; and
      the clamping face is inclined slightly relative to the displacement path, so that when the two locating parts are pushed together the clamping face moves progressively closer to the locating face of the clamping element.

2. A vertebral body replacement implant according to claim 1, wherein the inclination of the clamping face relative to the displacement path is between 1° and 10°.

3. A vertebral body replacement implant according to claim 2, wherein the inclination of the clamping face relative to the displacement path is between 1° and 3°.

4. A vertebral body replacement implant according to claim 1, wherein:
   the locating face, faces the clamping face; and
   an inclination of the locating face differs from that of the clamping face in such a way that the clamping element presses only at an edge of the locating face against the clamping face.

5. A vertebral body replacement implant according to claim 4, wherein the locating face is disposed parallel to the displacement path.

6. A vertebral body replacement implant according to claim 1, wherein the locating face faces the clamping face and moves into abutment with the clamping face and is so small that the locating face, as it is pressed against the clamping face, digs into said clamping face.

7. A vertebral body replacement implant according to claim 6, wherein the clamping element is an attachment screw.

8. A vertebral body replacement implant according to claim 1, wherein:
   the locating face faces the clamping face; and
   an inclination of the locating face relative to the displacement path corresponds to the inclination of the clamping face.

9. A vertebral body replacement implant according to claim 1, wherein:
   the clamping element is guided displaceably in a guide of said one of the bottom and top locating parts, and
   an adjusting screw is provided for displacement of the clamping element, said adjusting screw extending into the guide and abutting against the clamping element.

10. A vertebral body replacement implant according to claim 9, wherein the clamping element takes a form of a ring or a circular-cylindrical disk, a central axis of which is disposed parallel to the direction of displacement of the clamping element in the guide.

11. A vertebral body replacement implant according to claim 10, wherein a laterally projecting guide connection piece is disposed on said one of the bottom and top locating parts, an inner wall of said guide connection piece forming the guide for the clamping element and into which the adjusting screw may be screwed.

12. A vertebral body replacement implant according to claim 11, wherein a hydraulic conduit extends through a through-channel of the adjusting screw and through a central opening of the clamping element into an interior of said one of the bottom and top locating parts.

13. A vertebral body replacement implant according to claim 1, wherein the clamping face of the other of the bottom and top locating parts is formed by a base of a lateral recess in a side wall of the other of the bottom and top locating parts.

14. A vertebral body replacement implant according to claim 1, wherein both of the locating parts are displaceable telescopically relative to one another along the displacement path.

15. A vertebral body replacement implant comprising:
   a bottom locating part for positioning against a lower vertebral body,
   a top locating part for positioning against an upper vertebral body, both locating parts being steplessly displaceable relative to one another along a displacement path so that the height of the vertebral body replacement implant is variable,
   a clamping device for fixing the two locating parts in any desired intermediate position along the displacement path, said clamping device having a clamping element that is mounted on one of the bottom and top locating parts so as to be variable in position and can be pressed towards a clamping face on the other of the bottom and top locating parts, wherein:

the clamping face is inclined slightly relative to the displacement path, so that when the two locating parts are pushed together the clamping face moves progressively closer to the clamping element;

the clamping element is guided displaceably in a guide of said one of the bottom and top locating parts;

an adjusting screw is provided for displacement of the clamping element, said adjusting screw extending into the guide and abutting against the clamping element; and the clamping element takes a form of a ring or a circular-cylindrical disk, a central axis of which is disposed parallel to the direction of displacement of the clamping element in the guide.

16. A vertebral body replacement implant comprising:

a bottom locating part for positioning against a lower vertebral body, a top locating part for positioning against an upper vertebral body, both locating parts being steplessly displaceable relative to one another along a displacement path so that the height of the vertebral body replacement implant is variable, a clamping device for fixing the two locating parts in any desired intermediate position along the displacement path, said clamping device having a clamping element that is mounted on one of the bottom and top locating parts so as to be variable in position and can be pressed towards a clamping face on the other of the bottom and top locating parts, wherein:

the clamping face is inclined slightly relative to the displacement path, so that when the two locating parts are pushed together the clamping face moves progressively closer to the clamping element; and the clamping face of the other of the bottom and top locating parts is formed by a base of a lateral recess in a side wall of the other of the bottom and top locating parts.

* * * * *